US009347953B2

(12) United States Patent
Bastia et al.

(10) Patent No.: US 9,347,953 B2
(45) Date of Patent: May 24, 2016

(54) METHOD FOR THE DIAGNOSIS OF A CARCINOMA AND USES THEREOF

(75) Inventors: Filippo Bastia, Sozzigalli di Soliera (IT); Donato Altomare, Giovinazzo (IT); Alfredo Di Leo, Monopoli (IT); Maria Teresa Rotelli, Noicattaro (IT); Michele Barone, Bari (IT)

(73) Assignee: THD S.p.A., Correggio (IT)

( * ) Notice: Subject to any disclaimer, the term of this patent is extended or adjusted under 35 U.S.C. 154(b) by 163 days.

(21) Appl. No.: 13/991,715

(22) PCT Filed: Dec. 6, 2010

(86) PCT No.: PCT/IT2010/000484
§ 371 (c)(1),
(2), (4) Date: Aug. 8, 2013

(87) PCT Pub. No.: WO2012/077139
PCT Pub. Date: Jun. 14, 2012

(65) Prior Publication Data
US 2013/0316361 A1 Nov. 28, 2013

(51) Int. Cl.
*C12Q 1/68* (2006.01)
*G01N 33/53* (2006.01)
*G01N 33/566* (2006.01)
*G01N 33/574* (2006.01)
*G01N 33/68* (2006.01)
*G01N 33/50* (2006.01)
*C12N 5/077* (2010.01)
*C12N 5/0775* (2010.01)
*C12N 5/0789* (2010.01)

(52) U.S. Cl.
CPC ........ *G01N 33/6893* (2013.01); *G01N 33/5073* (2013.01); *G01N 33/57419* (2013.01); *G01N 33/57484* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 2003/0186439 | A1* | 10/2003 | Nakauchi et al. | 435/370 |
| 2004/0006003 | A1* | 1/2004 | Rodgers et al. | 514/7 |
| 2005/0233449 | A1* | 10/2005 | Lee et al. | 435/370 |
| 2009/0202544 | A1 | 8/2009 | Suciu-Foca et al. | |

FOREIGN PATENT DOCUMENTS

| CN | 1222193 A | 7/1999 |
| CN | 101669031 A | 3/2010 |
| CN | 102686723 A | 9/2012 |
| JP | 2004519475 A | 7/2004 |
| WO | 97/33995 A2 | 9/1997 |
| WO | 02/067760 A2 | 9/2002 |
| WO | 2004/024957 A2 | 3/2004 |
| WO | 2005/023300 A2 | 3/2005 |
| WO | 2005/043165 A2 | 5/2005 |
| WO | 2006/020684 A2 | 2/2006 |

OTHER PUBLICATIONS

Young and Black, The Anatomical Record, Part A, vol. 276A, pp. 75-102.*
Chen et al (Cytotherapy, 2006, vol. 8, pp. 381-389).*
Abe et al (Journal of Immunological Methods, 2002, vol. 270, pp. 227-233).*
Demel et al (Journal of Experimental and Clinical Cancer Research, 2004, vol. 23, pp. 465-468).*
Silva, et al., "Detection of Epithelial Tumour RNA in the Plasma of Colon Cancer Patients is Associated With Advanced Stages and Circulating Tumour Cells", Gut, British Medical Association, London, UK, vol. 50, No. 4, Apr. 1, 2002, pp. 530-534.
Gervasoni, et al., "Molecular Signature Detection of Circulating Tumor Cells Using a Panel of Selected Genes", Cancer Letter, New York, NY, USA, vol. 263, No. 2, May 18, 2008, pp. 267-279.
Jaw-Yuan Wang, et al., "Molecular Detection of Circulating Tumor Cells in the Peripheral Blood of Patients With Colorectal Cancer Using RT-PCR: Significance of the Prediction of Postoperative Metastasis", World Journal of Surgery; Official Journal of the International Society of Surgery, Springer-Verlag, Netherlands, vol. 30, No. 6, May 4, 2006, pp. 1007-1013.
Stathopoulou, et al., "Molecular Detection of Cytokeratin-19-Positive Cells Operable Breast Cancer: Evaluation of Their Prognostic Significance", Journal of Clinical Oncology, American Society of Clinical Oncology, USA, vol. 20, No. 16, Aug. 15, 2002, pp. 3404-3412.
Michel Martine, et al., "Keratin 19 as a Biochemical Marker of Skin Stem Cells in Vivo and in Vitro: Keratin 19 Expressing Cells Are Differently Localized in Function of Anatomic Sites, and Their Number Varies With Donor Age and Culture Stage", Journal of Cell Science, Cambridge University Press, London, GB, vol. 109, No. 5, Jan. 1, 1996, pp. 1017-1028.
Tsouma Aikaterini, et al., "Circulating Tumor Cells in Colorectal Cancer: Detection Methods and Clinical Significance", Anticancer Research, vol. 28, No. 6B, Nov. 2008, pp. 3945-3960.
Szabo Pavol et al., "Mouse 3T3 fibroblasts under the influence of fibroblasts isolated from stroma of human basal cell carcinoma acquire properties of multipotent stem cells", Biol. Cell (2011), May 2011, vol. 103, No. 5., pp. 233-248.

* cited by examiner

*Primary Examiner* — Karen Canella
(74) *Attorney, Agent, or Firm* — Jeffrey N. Townes; LeClairRyan

(57) ABSTRACT

The present invention relates to a method for diagnosing a carcinoma or a residual disease associated thereto, or for the prognosis of a carcinoma, or for monitoring the effectiveness of an anti-tumour therapy directed against a carcinoma, or for monitoring the follow-up of an individual affected by a carcinoma, in particular colorectal carcinoma, carcinoma of the stomach, mammary carcinoma, pulmonary carcinoma or carcinoma of the prostate, carcinoma of the liver, carcinoma of the ovary, carcinoma of the kidney, carcinoma of the thyroid, carcinoma of the bladder or carcinoma of the pancreas. The method of the invention consists in placing adult stem cells in contact with a sample of a haemo-derivative of the individual to be analyzed and in verifying the expression of at least an epithelial marker in the stem cells by means of immunofluorescence, immunohistochemistry, ELISA or RT-PCR.

17 Claims, 9 Drawing Sheets

METHOD FOR THE DIAGNOSIS OF A CARCINOMA AND USES THEREOF

Figure 1:
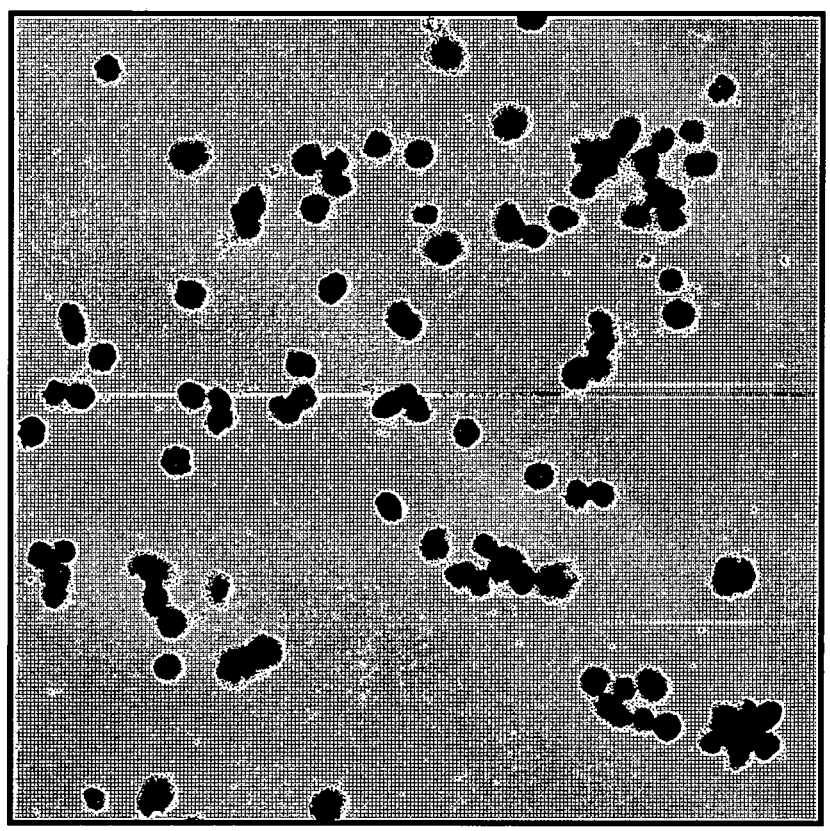

The present invention relates to a method for diagnosing a carcinoma or a residual disease associated to a carcinoma, or for the prognosis of a carcinoma.

Further, the method of the present invention enables monitoring the effectiveness of a teraphy directed against a carcinoma or a follow-up of an individual affected by a carcinoma.

A carcinoma is a tumour of epithelial origin characterised by high incidence.

Some types of carcinoma, such as colorectal carcinoma, mammary carcinoma, lung carcinoma, hepatic or prostatic carcinoma, represent some of the tumours at present most widespread among the population.

In particular, the colorectal carcinoma is estimated to be the second/third cause of decease through neoplasia. The above epidemiological datum is rather disconcerting, especially if it is related to the considerable improvements which have been achieved in recent years in diagnosis and surgical and curative treatment of this type of tumour.

The colorectal carcinoma is a cancer characterised by a usually slow progression, and therefore its early diagnosis is fundamentally important for the survival of the affected individual.

Screening has always been a crucial tool for early diagnosis of carcinoma of the colon and rectum, as well as for defining the best curative therapy. The most commonly-used screening method is testing for occult blood in the faeces.

An individual who has tested positive in this type of examination can be subjected to further examinations (for example colonoscopy or opaque clisma) with the aim of defining the nature of the bleeding.

The bleeding might in fact be due to a different or secondary condition with respect to colorectal carcinoma. For example, the bleeding might be associated to: haemorrhoids, diverticulitis and diverticulosis, chronic inflammatory diseases, appendicitis, intestinal ischemia or irritable bowel, intestinal tuberculosis, endometriosis or the presence of extraneous bodies, or even pathologies of the first tract of the digestive apparatus such as oesophago gastro duodenitis, accompanied by mucous membrane erosion phenomena, ulcerous diseases or angiodysplasia. A promising new development in screening of colorectal carcinoma is represented by the faecal DNA test which, however, is not yet a routine clinical practice. This test enables identification and quantisation of the mutated DNA sequences which are associated to the tumour (however only a small percentage of tumours are associated to these mutations). The quantised DNA in this type of test is directly proportional to the number of neoplastic cells present in the faeces. The cells derive from the process of exfoliation which accompanies both the onset and the evolution of colorectal cancer.

Colonoscopy, opaque clisma, PET and CT scans are some of the techniques associated and complementary to screening techniques. In particular, they serve to qualitatively and quantitatively evaluate both the zone of the colorectal lesion and the zone surrounding the lesion.

These techniques, though being invasive and quite expensive, are crucial, especially for the aim of planning the surgical intervention in detail; today this still represents the best therapeutic approach to cancer of the colon and rectum.

Following the surgical treatment, the affected individual is usually subjected to adyuvant therapies, in order to prevent recurrence.

These therapies consist in administering chemotherapy, together with, or without, radiotherapy.

The chemo-radiotherapy approach can be effected during the pre- or post-operatory stage. In the pre-operatory stage, a chemo-radiotherapy treatment might be useful to the aim of reducing the size of the tumour and, consequently, the seriousness of the surgical intervention.

In this regard, it is usually decided to adopt a conservative approach, with the objective of preventing excision of the anal sphincter and the elevator muscle of the anus during the surgical intervention.

Further, a pre-operatory chemo-radiotherapeutic treatment is useful for increasing the survival rates in this type of very invasive intervention.

Recently a genetic search (known as the K-RAS test) has been set up, which is very useful for the objective of predicting, during diagnosis, the possible response of the colorectal tumour to customised treatment for each affected individual.

This test comprises determining the K-RAS protein, which is responsible for transducing the signals related to proliferation and is therefore an important oncogen. In particular, the test determines whether the K-RAS protein has mutated or not.

Notwithstanding the huge advances made in the diagnosis and clinical treatment of colorectal carcinoma, at present 30% of individuals affected by a colorectal tumour in the early stages die because the disease propagates over only a few years (4-5 years) due to the persistence of microscopic residues of the disease.

In this context, the problem at the base of the present invention relates to the provision of a method for diagnosis (in particular early diagnosis) of a carcinoma or the residual disease associated thereto which obviates the drawbacks of the screening methods or diagnostic methods of the prior art.

In particular, it is desired to make available a diagnostic method of a carcinoma or the residual disease associated thereto which can be performed rapidly and which is less invasive and more specific and sensitive than conventional methods.

This problem is solved by a method for diagnosing a carcinoma or the residual disease associated thereto, or for the prognosis of a carcinoma or for monitoring the follow-up of an individual affected by a carcinoma, or for monitoring the effectiveness of an anti-tumour therapy, as delineated in the appended claims.

The method of the invention comprises placing isolated stem cells in contact with a sample of a haemo-derivative originating from the individual to be assessed.

Subsequently verification is made of whether the contact has induced expression of at least an epithelial marker by the stem cells. Stem cells which express the at lea an epithelial marker are stem cells that express an epithelial phenotype following the contact with the sample of a haemo-derivative.

The expression of at least an epithelial marker by the stem cells, following treatment with a sample of an individual's haemo-derivative, is indicative of the fact that the individual is affected by a carcinoma or has the residual disease associated thereto. Indeed, the presence of disease or residual disease implies the presence in the blood of the affected person of a factor which promotes differentiation, in the epithelial sense, of the stem cells.

Further, the determining of the expression of at least an epithelial marker by the stem cells placed in contact with a sample of a haemo-derivative of an individual is indicative of the effectiveness, the evolution and/or the outcome of a therapy directed against a carcinoma or against the residual disease associated to a carcinoma.

Finally, the expression of at least an epithelial marker by the stem cells placed in contact with a sample of a haemo-derivative of an individual is indicative of the evolution of a carcinoma and thus of its prognosis.

The determining of the expression of at least an epithelial marker by stem cells placed in contact with a sample of a haemo-derivative of an individual subjected to a therapy against a carcinoma (surgical or chemo-radiotherapy) enables monitoring the treatment follow-up. The method of the present invention can be performed rapidly and is not invasive with respect to known radiographic or endoscopic methods. In fact with only a simple blood sample the method enables diagnosis of a carcinoma or residual disease associated thereto, or enables prognosis of a carcinoma, or monitoring the effectiveness of an anti-tumour therapy directed against a carcinoma, or it enables monitoring the follow-up of an individual affected by carcinoma and subjected to therapeutic treatment.

Further, the method is characterised by a high specificity and sensitivity with respect to classic screening methods.

As has been specified, faecal occult blood testing and the faecal DNA test can easily give rise to false positives and false negatives (for example, subjects affected by haemorrhoids might result positive to the above test). The faecal occult blood test can give positive results even when an individual is affected by a non-neoplastic pathology, while the faecal DNA test (which among other things is not yet standardised in, clinical use) can give rise to a high number of false negatives because the mutations searched for are expressed only in a small percentage of the cases of carcinoma (for example, in 60% of colorectal tumours). Additionally, the faecal DNA test requires a sophisticated and expensive laboratory methodology.

The method of the present invention enables precise and reliable assigning of each sick subject to the correct category of risk and, consequently, facilitates the clinical personnel during the stage of identifying the most suitable treatment for the specific patient.

Figure 5:
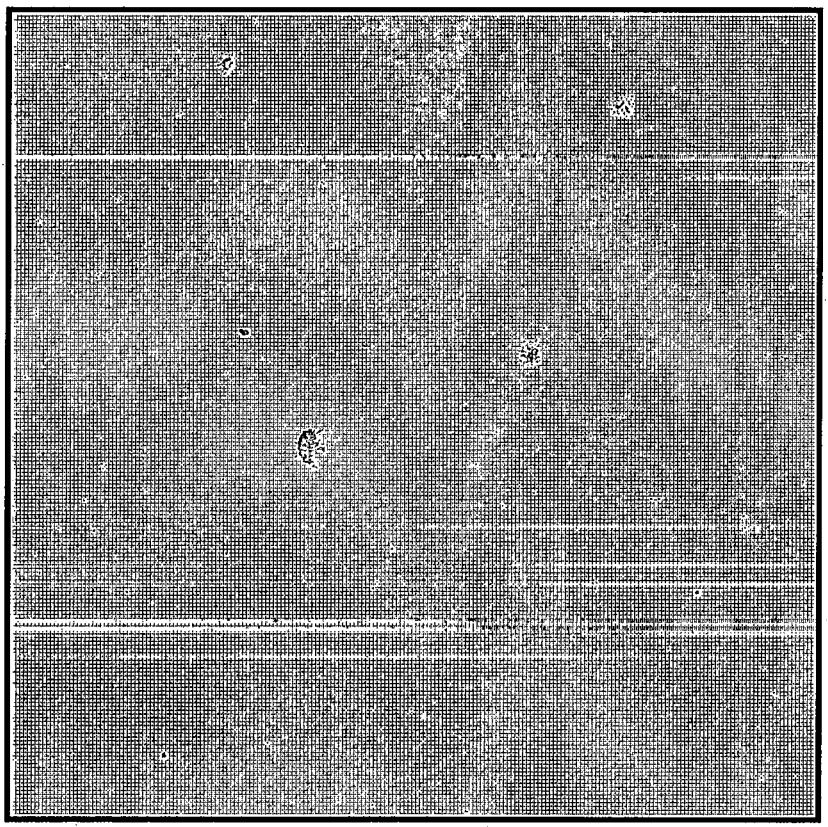
Figure 6:
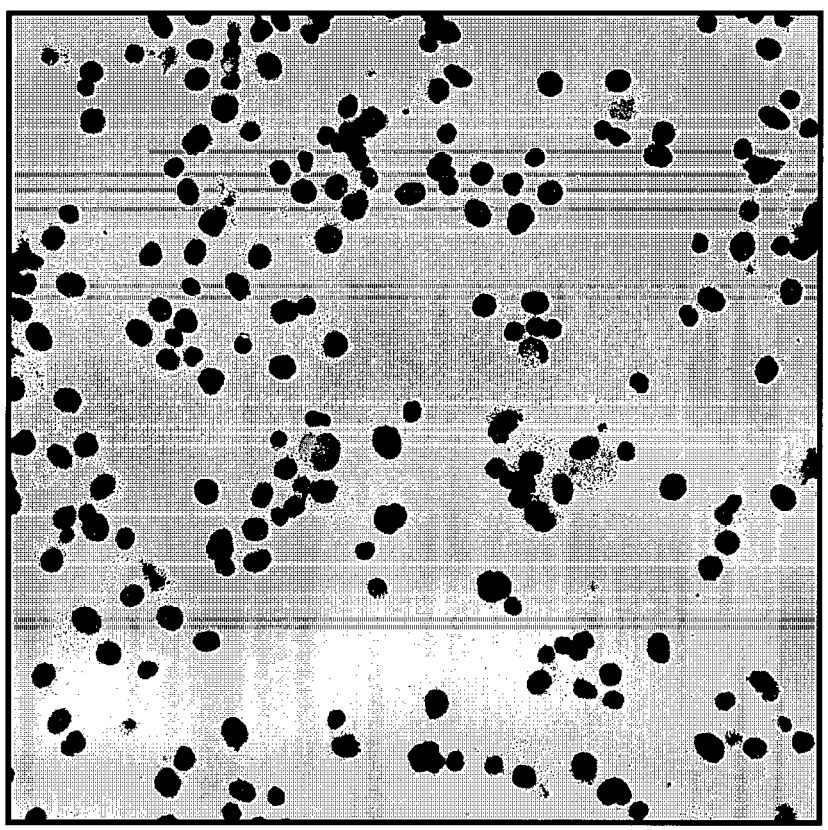
Figure 7:
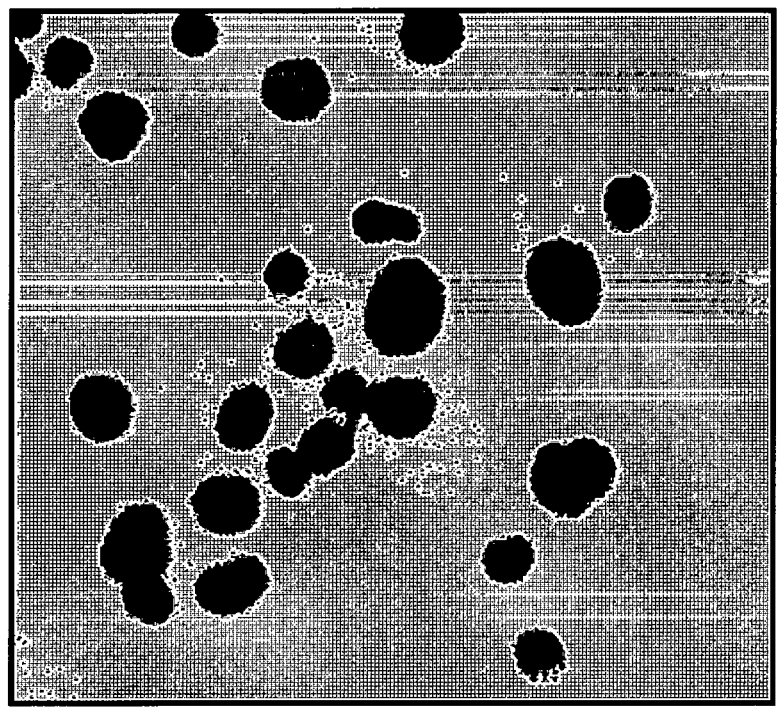
Figure 7:
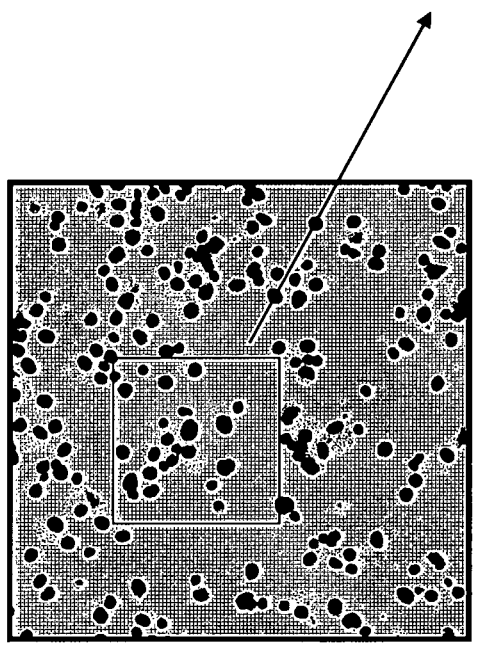
Figure 8:
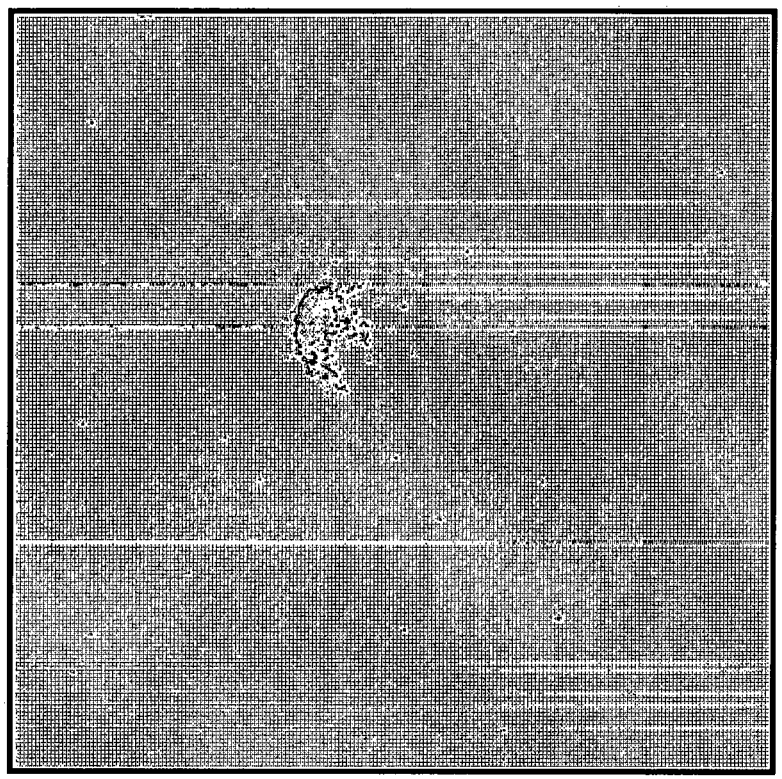
Figure 8:
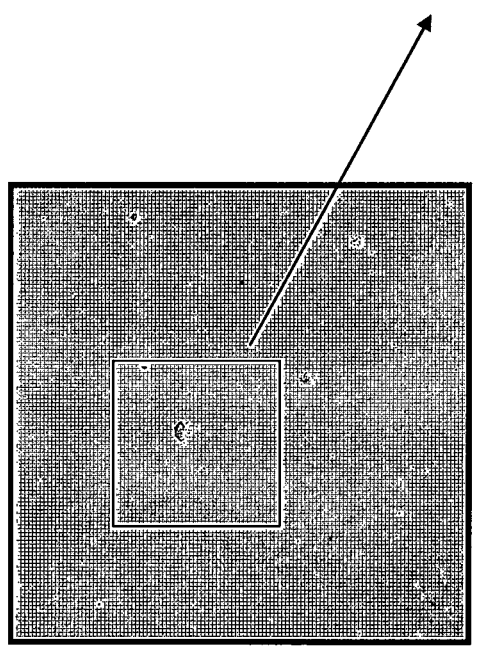
Figure 9:
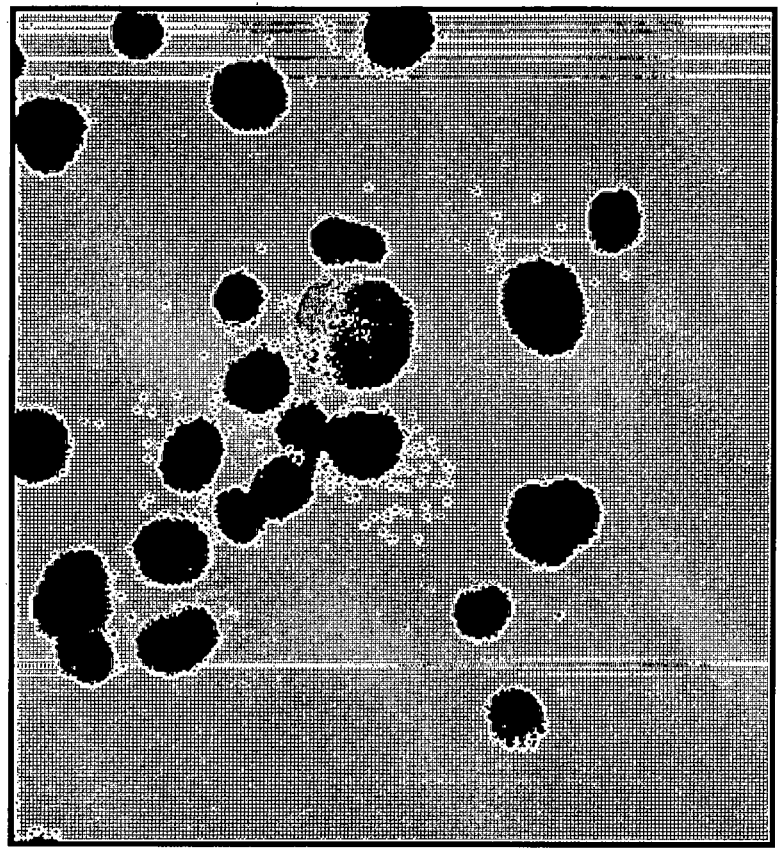
Figure 9:
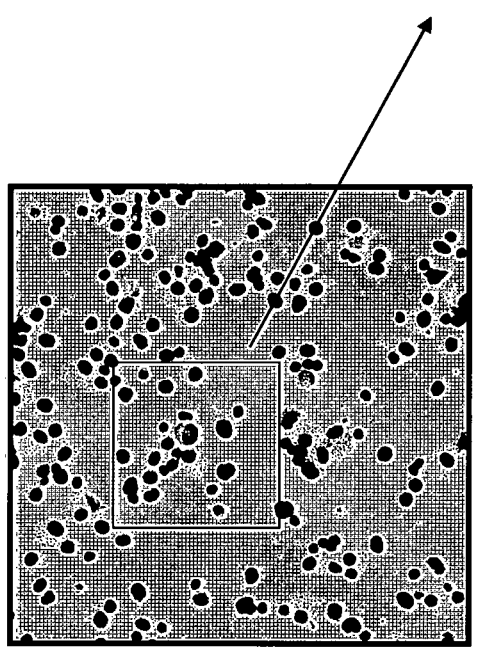

The invention is illustrated in detail herein below, with the aid of the accompanying figures, in which:

FIGS. 1-9 show the immuniofluorescence images of bone marrow cells cultivated in the presence of serum from a healthy individual (FIGS. 1-3) and an individual affected by carcinoma (FIGS. 4-9). FIGS. 7-9 are an enlargement, respectively, of FIGS. 4-6.

Figure 2:
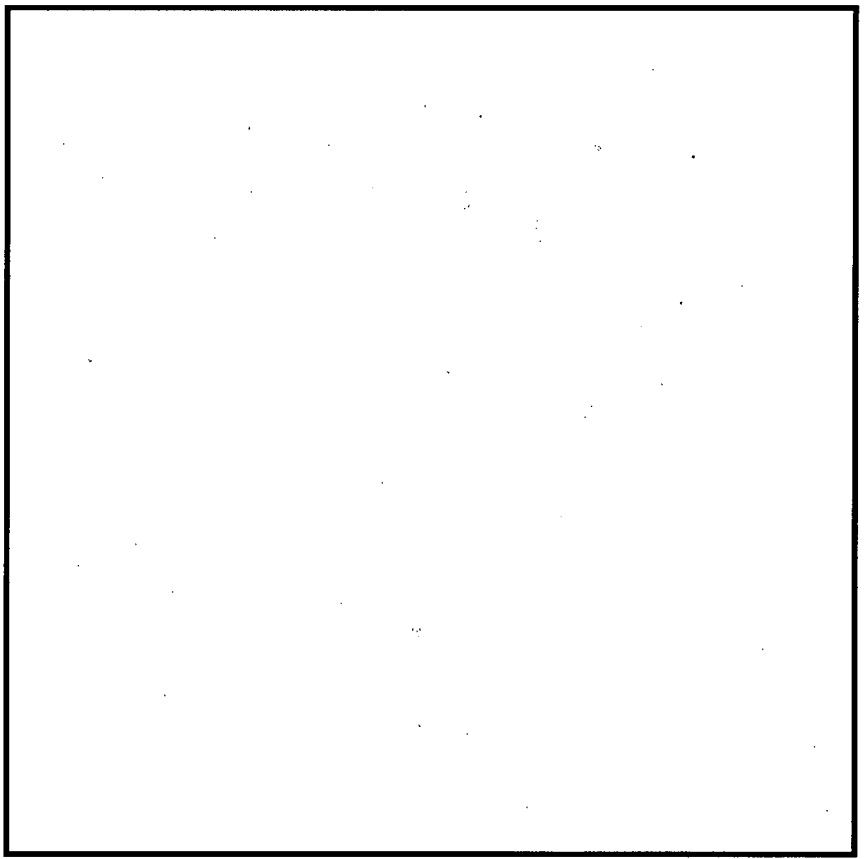
Figure 3:
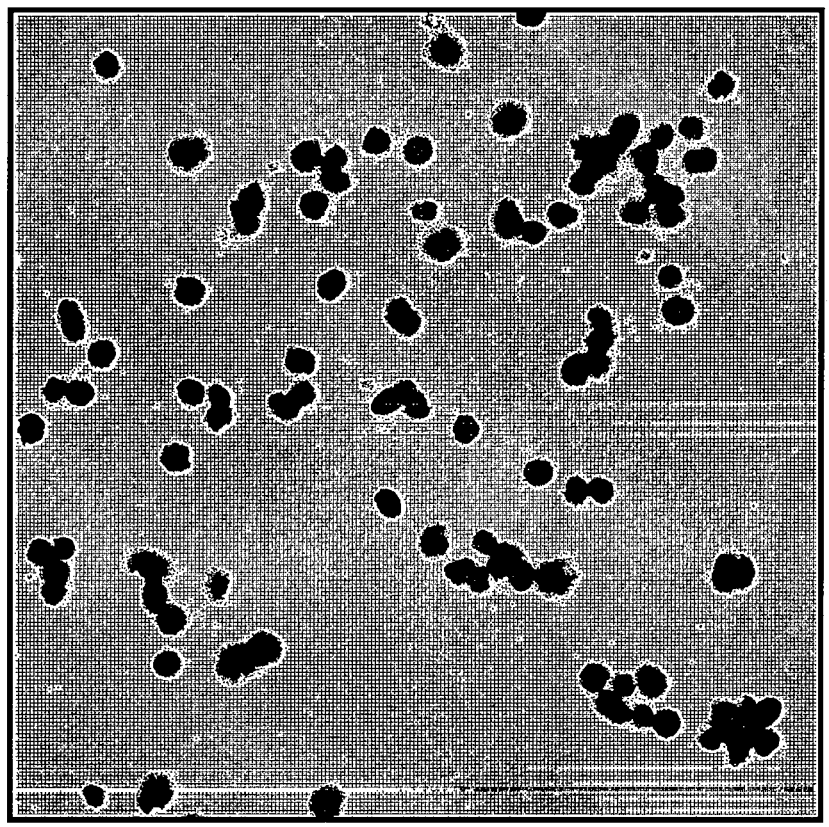
Figure 4:
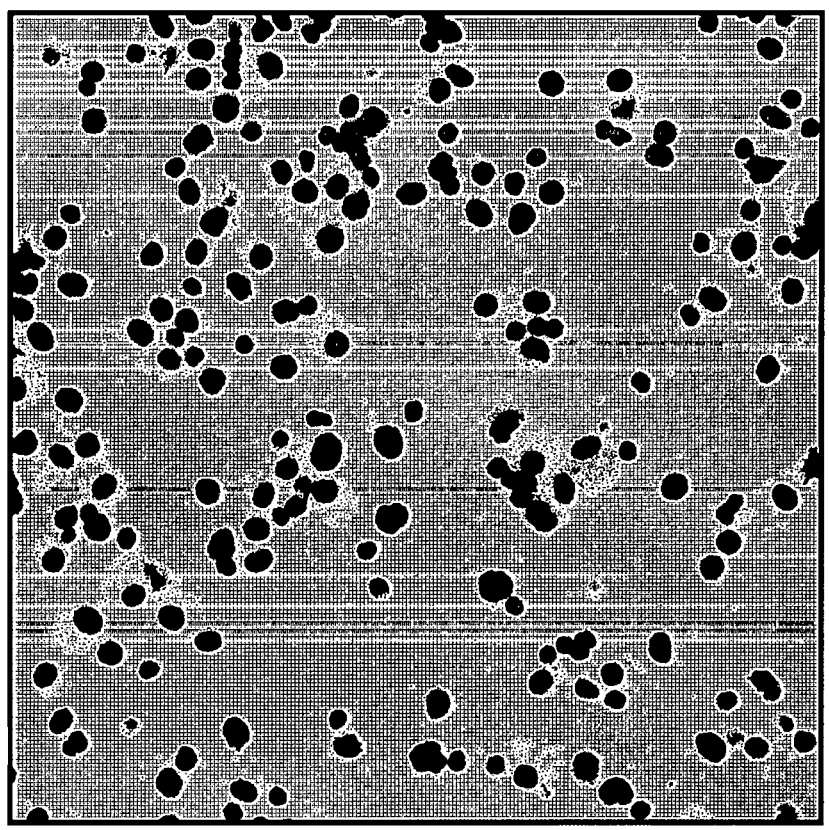

The black signal in FIGS. 1, 4 and 7 defines the localisation of the nuclear marker TO-PRO (which marks all the cell nuclei), while in FIGS. 2, 5 and 8 the grey signal defines the marker CK-19. FIGS. 3, 6 and 9 report the superposing of the nuclear signal and the CK-19 signal. The images clearly show that only the cells placed in contact with the serum of the individual affected by carcinoma (FIGS. 4-9) are positive for CK-19 (FIGS. 5 and 8); FIG. 2 is indeed completely lacking in signals. Further, it is evidenced that the CK-19 signal is cytoplasmic.

The method of the present invention is applied for the diagnosis, in an individual, of a carcinoma or residual disease associated thereto, or for defining, in an individual, the prognosis of a carcinoma, or for monitoring the follow-up for an individual affected by a carcinoma, or for monitoring the effectiveness of an anti-tumour therapy directed against a carcinoma. The method of the invention comprises steps of:

(i) placing isolated stem cells in contact with an isolated sample of a haemo-derivative, and (ii) verifying or evaluating the expression of at least an epithelial marker in said stem cells.

The method of the invention is based on the scientific rationale that a carcinoma, for example a primary lesion, is able to release, in the individual affected by the tumour, signals which induce differentiation into epithelial cells of stem cells such as for example those residing in the bone marrow. These cells have been termed DECs—Disseminated Epithelial Cells). DECs do not have. the identity of the primary tumour (for example they do not exhibit the same mutations), thus they derive from resident cells (of mesenchymal derivation) which have differentiated into epithelial cells; in particular, it has been shown that this differentiation is guided by signals released by primary tumour cells.

The method of the present invention enables diagnosis of a carcinoma in an early stage or a carcinoma in an advanced stage. The carcinoma is preferably one of the following: colorectal carcinoma, carcinoma of the stomach, mammary carcinoma, lung carcinoma, prostate carcinoma, carcinoma of the ovary, carcinoma of the liver, carcinoma of the kidney, carcinoma of the thyroid, carcinoma of the bladder or carcinoma of the pancreas.

Further, the method of the present invention relates to diagnosis of the residual disease, preferably the microscopic residual disease associated to a carcinoma.

By residual disease is intended the persistence of the carcinoma (for example, micro-metastasis or disseminated tumoral cells) which are not clinically identifiable, or not identifiable with ordinary instrumental diagnosis (for example CT scans, magnetic resonance, ultra-sound examinations, etc.).

The follow-up for an individual affected by carcinoma relates to the stage following the therapy (surgical or chemo-radiotherapy) to which an individual affected by a carcinoma or by the residual disease associated thereto has been subjected.

The method of the present invention is performed in vitro; in particular, it is performed on isolated samples of haemo-derivatives (otherwise definable as derivatives of the blood). The sample of haemo-derivatives which is used for the test is serum or plasma.

For the aims of the present invention, the stem cells to which reference is made are, preferably, adult stem cells, and more preferably are pluripotent stem cells, and still more preferably are selected from among mesenchymal stem cells, $CD133^+$ cells (i.e. cells expressing protein CD133), $CD44^+$ cells, $CD90^+$ cells, $CD29^+$ cells, $CD105^+$ cells, $CD117^+$ cells, $CD56^+$ cells and $CD73^+$ cells.

The at least an epithelial marker, whose expression is measured by the method of the invention, is at least a cytokeratin.

Cytokeratins are filament proteins that are especially useful in the field of oncological diagnosis. They are expressed by epithelial cells and therefore are useful markers in detecting the presence of malignant epithelial tumours.

The cytokeratin used in the method of the present invention is preferably selected from: cytokeratin 18, 19, 20 and 21 (CK-18, CK-19, CK-20 and CK-21), more preferably the cytokeratin is CK-19.

Step (i), which comprises placing stem cells in contact with a sample of a haemo-derivative, comprises a stage of seeding the stem cells on a support suitable for cell growth (for example a dish, a flask, etc.) and a stage of dilution of the sample of a haemo-derivative of the individual in the culture medium suitable for the stem cells used. The culture medium can be, for example, alpha-MEM or StemSpan, preferably enriched with growth factors.

Dilution of the sample of a haemo-derivative in the culture medium varies from 1:2 to 1:20, and preferably varies from 1:4 to 1:8.

Once diluted in the culture medium, the haemo-derivative sample is added to the stem cells. The stem cells are grown in the terrain containing the haemo-derivative sample for a time that varies from 48 to 180 hours, preferably from 90 to 150 hours.

During this time period, the stem cells differentiate into epithelial cells only if the haemo-derivative sample contains one or more suitable differentiating signals. The differentiating signals are released into circulation by a carcinoma and are therefore present in the haemo-derivative sample only if the individual is affected by a carcinoma.

Once this period of time has passed, it is possible to proceed with the verification of the presence of the differentiated stem cells (into epithelial cells) in the culture, evaluating the expression of at least an epithelial marker in the stem cells (if any) that have undergone differentiation.

Before proceeding with the determination of the expression of at least an epithelial marker, the sample of haemo-derivative diluted in the culture medium is preferably removed from the cells.

The expression is determined using the common detecting methods, known in the sector. Non-limiting examples of these methods are: immunofluorescence, immunocytochemistry, ELISA (Enzyme-Linked ImmunoSorbent Assay), RT(Reverse Transcriptase)—PCR (Polymerase Chain Reaction); preferably the RT-PCR is a real-time test. The preferred methods as regards the method of the invention are immunofluorescence and RT-PCR.

The method of the invention can be realised both on single haemo-derivative samples and on groups of haemo-derivative samples. For example the stem cells can be distributed on a multi-well plate having 6, 12, 24, 36, 48 or 96 wells. The sample of diluted haemo-derivative in the appropriate culture medium is added to each well, and is left in contact with the cells for the above-prescribed time.

The stage of determining at least an epithelial marker can be, therefore, realised contemporaneously in the various wells. In this way the method of the invention can be applied on groups of samples of haemo-derivatives, even originating from different patients.

The use of a multi-well system enables both manual reading of the positive signal at the microscope, and automated reading, for example using an ELISA reader or a fluorometer.

In a case in which step (ii) of determining the expression of at least an epithelial marker is realised by means of ELISA, the stem cells that have been in contact with the sample of a haemo-derivative are subjected to a stage of lysis.

The lysis stage comprises treatment of the cells with a suitable solution which causes breakage of the integrity of the cell membrane and enables recuperation of the total proteins of the cells, i.e. it enables collecting a lysate of cell proteins.

Said lysate of cell proteins is representative of cellular identity and its biological activity at the moment of lysis, and contains, if present, at least an epithelial marker expressed by the differentiated stem cells, i.e. the stem cells that have differentiated into epithelial cells following contact with a sample of a haemo-derivative of an individual affected by a carcinoma or by the residual disease associated thereto.

The sample of protein lysate obtained from the cells placed in contact with the sample of a haemo-derivative is subjected to an ELISA assay with the aim of verifying and quantifying the presence (and therefore the expression) in the protein lysate of at least an epithelial marker.

The determination of the expression of at least an epithelial marker via ELISA is realised, for example, on multi-well plates, preferably on plates having 96 wells. Said plates can be pre-treated with at least an antibody directed against said at least an epithelial marker (primary antibody) with the aim of enabling adsorption of the antibody in the plate. Alternatively the adsorption of the primary antibody can be realised extemporaneously during the progress of the method of the invention. An aliquot of protein lysate is placed in contact with the primary antibody adsorbed on the plate.

Said antibody will bond to the at least an epithelial marker which may be expressed by the differentiated stem cells following contact with the sample of haemo-derivative.

The determination of the said bond is realised by use of a new antibody directed against the at least an epithelial marker (second primary antibody) or by use of an antibody directed against the primary antibody (secondary antibody). Both the antibodies are preferably joined with an enzyme (for example diaminobenzidine or alkaline phosphatase or HRP) which is able to react with a suitable substrate (added extemporaneously during the performing of the method) to determine a coloration of the analysed sample.

The intensity of the coloration is determined using an appropriate instrument and is indicative of the quantity of the at least an epithelial marker expressed by any differentiated stem cells in epithelial cells following contact with the at least a sample of a haemo-derivative of an individual affected by a carcinoma or by the residual disease associated thereto.

Step (ii), verifying the expression of at least an epithelial marker in the stem cells placed in contact with a sample of a haemo-derivative, can be realised by means of PCR, preferably by RT-PCR, still more preferably by RT-PCR in real time.

In this case, for the amplification of the DNA, or the cDNA (obtained by inverse transcription of the messenger corresponding to the gene of interest) one or more pairs of oligonucleotides can be used, each oligonucleotide of the pair being able to bond to one of the two DNA filaments. After the bonding of the oligonucleotide pair to each DNA filament it will be possible to amplify the DNA sequence interposed between them using classic PCR. Each oligonucleotide of the pair is preferably constituted by 15-30 nucleotides. Said oligonucleotide can be designed on the basis of the gene sequence of interest, using, for example, algorithms at present available for generating oligonucleotides starting from a sequence of interest. The gene of interest is preferably the one which encodes for a cytokeratin, preferably for cytokeratin 18, 19, 20 or 21.

When step (ii) of verifying the expression of at least an epithelial marker in the stem cells placed in contact with a haemo-derivative sample, is realised by immunofluorescence, said stem cells are deposited on the slide with or without a fixative agent. Thereafter, they are placed in contact with a specific antibody for the at least an epithelial marker, possibly conjugated with a fluorochrome or an enzyme. In a case in which the specific antibody is free (i.e. not conjugated), in order to proceed to evidencing a second antibody is used, directed against the specific antibody, conjugated to a fluorochrome or an enzyme. Said antibody will bond to the at least an epithelial marker (if any) expressed by stem cells following contact with a haemo-derivative sample of an individual affected by a carcinoma or by the residual disease associated thereto.

Once this preparation has been performed, the expression of at least an epithelial marker by the differentiated stem cells is revealed under the microscope.

In the method of the present invention, the expression of at least an epithelial marker in the stem cells, after they have been placed in contact with an isolated sample of a haemo-derivative, is indicative of the presence of a carcinoma or a residual disease associated thereto.

Further, said expression is also indicative of the degree of progression of the carcinoma from which it is possible to deduce the prognosis of the pathology.

The method of the invention enables follow-up of an individual affected by a carcinoma or by the residual disease associated thereto and therapeutically treated such as to eliminate the tumour. When the determination of the expression of the at least an epithelial marker by a sample of stem cells is effected using samples of haemo-derivatives obtained in steps that are subsequent to a therapeutic treatment (able to eliminate a tumour), to which an individual affected by carcinoma has been subjected, it is possible to monitor any eventual reappearance of the illness.

This possibility guarantees a rapid therapeutic intervention in a case in which during the stages subsequent to the therapeutic treatment of said individual affected by carcinoma, the expression of at least an epithelial marker is determined.

In this situation, in the haemo-derivative sample obtained in the successive stage of the therapeutic treatment to which said individual has been subjected (and which stage has eliminated the tumour), there would be new signals capable of inducing the differentiation of the stem cells into epithelial cells, indicating the fact that the individual is newly affected by a tumour or the residual disease associated thereto.

Finally, the method of the invention is also used for monitoring the effectiveness of a therapeutic anti-tumour treatment, in particular a chemo/radiotherapy treatment. In this case the method comprises comparison of the levels of expression of at least an epithelial marker of the stem cells after they have been placed in contact with a sample of a haemo-derivative of a sick individual in various stages of the therapeutic treatment to which the individual is subjected.

The alteration of the said levels of expression is indicative of the progression of the treatment itself. For example, a lowering in the levels of expression in advanced stages of the therapeutic treatment with respect to the initial stages is indicative of the effectiveness of the treatment. The method of the present invention is characterised by a specificity which varies from 60% to 100%, preferably from 70% to 90%.

As for the sensitivity of the method, it varies from 60% to 100%, preferably from 70% to 90%.

In a further embodiment, the method of the present invention is used in combination with other diagnostic/prognostic methods presently in use with the aim of integrating the techniques of the investigation. For example, the method can be applied in combinatibn with: colonoscopy, opaque clisma, faecal DNA testing and other possible investigations with the aim of being able to define an ad hoc therapeutic/prognostic approach for each single patient.

The completion of the clinical data originating from the known investigation techniques and the method of the present invention facilitates and improves the definition of the personalised therapeutic approach, which is very advantageous in treating a carcinoma.

A further aspect of the present invention relates to a kit comprising: at least an antibody directed against at least an epithelial marker (defined the primary antibody) or at least a pair of oligonucleotides for amplification of the cDNA or DNA of at least an epithelial marker; and/or at least a sample of stem cells; and/or a means for cultivating said stem cells. Said antibody directed against an epithelial marker is directed against a cytokeratin, preferably cytokeratin 18, cytokeratin 19, cytokeratin 20 or cytokeratin 21; more preferably the antibody is directed against cytokeratin 19.

Said antibody directed against an epithelial marker can be directly conjugated with a fluorochrome suitable for determination by means of common immunofluorescence techniques (for example Texas Red, Fluorescein (FITC), Ficoerythrin (PE), Tetramethyl Rhodamine Isothiocyanate (TRITC)), or said antibody is conjugated with an appropriate molecule, for example a protein, which enables determination using common colorimetric assays, for example by immuno histochemistry (by way of example said molecule can be daminobenzidrine or alkaline phosphatase or HRP).

Alternatively, the primary antibody is free. In this case, for determination a secondary antibody is used (directed against the primary) conjugated as described above. In the latter case, the kit further comprises a secondary antibody, i.e. an antibody directed against the primary antibody. Said secondary antibody is conjugated with a fluorochrome or an enzyme for determination.

The kit can further comprise instrumentation that can be single-use, sterile or sterilisable, for performing the method, for example a multi-well plate that has been pretreated (or not) with at least an antibody directed against the at least an epithelial marker.

The kit can further comprise useful substances for carrying out the determination method, for example a solution that is suitable for performing retro-transcription and amplification of the cDNA/DNA of at least an epithelial-type marker, comprising, for example, a reverse transcriptase, an enzyme for amplification of the DNA, salts, a mixture of nucleotides, surfactants or reducing agents.

Further, said substances can be, for example, solutions for cell lysis or washing, fixing, blocking, neutralisation or determination solutions.

Said kit is useful for diagnosing whether an individual is affected by a carcinoma or has a residual disease associated to a carcinoma, or for defining a prognosis in an individual affected by a carcinoma.

Further, said kit can be used for monitoring the effectiveness of a therapeutic treatment or the follow-up for an individual affected by carcinoma. In other words, the kit is used for realising the method of the invention.

EXAMPLE

Cells

Mononuclear human cells from the bone marrow (BM-MNCs) were purchased from STEMCELL Technologies.

On arrival the BM-MNCs were thawed, using 250 µl of Dnase I (1 mg/ml) in a culture medium containing 10% serum (bovine foetal serum for mesenchymal stem cells, StemCell Technologies) and penicillin/streptomycin 1× (StemCell Technologies).

The cells were cultured for a minimum of 3 days before setting up the stimulation experiments with the serum samples.

The expansion medium used for cultivating and amplifying the cells was constituted by Alpha MEM or StemSpan SFEM (Serum-Free Expansion Medium, StemCell Technologies) enriched with growth factors (StemSpan CC100-StemCell Technologies).

BM-MNC Stimulation Assays with Human Serum.

The serum was obtained from blood samples originating from individuals affected by colo-rectal carcinoma and from healthy donors.

19 individuals affected by carcinoma were tested with the method of the invention, and in more detail the individuals were affected by different-stage adenocarcinoma.

Table 1 summarises the clinical data relative to 18 individuals affected by carcinoma.

Table 1 also reports the experimental data relating to individual healthy donors. In particular, 12 healthy samples were analysed (S 1-12).

The Table Reports:
1) the histological diagnosis of the tumour;
2) the international tumour staging (denoted by pTNM, in which T is the degree of invasion of the visceral tunica, N the state of the lymph nodes, M the presence or not of metastasis); and
3) the positivity for CK-19 (indicated with BM-MNC CK-19[30]), i.e. the presence of cells expressing CK-19.

TABLE 1

| Sample | Histical diagnosis | pTNM | BM-MNC CK-19+ |
|---|---|---|---|
| CCR-1 | Moderately differentiated adenocarcinoma - Mucinous | | + |
| CCR-2 | Well-differentiated adenocarcinoma - Post radio-chemo | | + |
| CCR-3 | Well-differentiated adenocarcinoma | T3N1M1 | + |
| CCR-4 | Moderately diffuse adenocarcinoma-Hepatic metastasis | T3N2M1 | + |
| CCR-5 | Well-differentiated adenocarcinoma on villous adenoma (benign tumour with high risk of malignant degeneration) | T3N0Mx | + |
| CCR-6 | Moderately-differentiated adenocarcinoma | T3N0Mx | + |
| CCR-7 | Poorly-differentiated adenocarcinoma | T3N3Mx | + |
| CCR-9 | Well-diffuse adenocarcinoma - Tubular adenoma - Cholecystitis | T3N0Mx | + |
| CCR-11 | Moderately-differentiated adenocarcinoma | | + |
| CCR-12 | Moderately-differentiated adenocarcinoma | | + |
| CCR-16 | Moderately-differentiated adenocarcinoma | T3N2M1 | + |
| CCR-18 | Poorly-differentiated adenocarcinoma | | + |
| CCR-20 | Moderately-differentiated adenocarcinoma | T3N2Mx | + |
| CCR-21 | Well-differentiated adenocarcinoma | T3N0Mx | + |
| CCR-22 | Moderately-differentiated adenocarcinoma | T3N2Mx | + |
| CCR-23 | Moderately-differentiated adenocarcinoma - Mucinous | T4N2Mx | + |
| CCR-24 | Well-differentiated adenocarcinoma | T2N0Mx | + |
| CCR-25 | Moderately-differentiated adenocarcinoma - Mucinous | T4N3Mx | + |
| S-1 | | | − |
| S-2 | | | − |
| S-3 | | | − |
| S-4 | | | − |
| S-5 | | | − |
| S-6 | | | + |
| S-7 | | | − |
| S-8 | | | + |
| S-9 | | | − |
| S-10 | | | + |
| S-11 | | | − |
| S-12 | | | − |

Each serum sample was sterilised with appropriate filters having pores of 0.22 μm (Corning Costar).

About 100000 cells in total were seeded in each well (about 100000 cellule/cm$^2$). A quantity of 250 μl of serum was added in 1250 μl of culture medium (i.e. the serum was diluted at 1:6).

After 120 hours of incubation at 37° C., in an atmosphere containing 5% $CO_2$, the cells were recuperated and processed for determining the CK19 signal by immunofluorescence.

All the experiments conducted were performed in duplicate.

Immunofluorescence

The BM-MNCs were detached from the support on which they had been cultured and were re-suspended in 100 μl of PBS. Then they were uniformly distributed on polarized slides and left to dry overnight at ambient temperature.

Then they were fixed to the slide in 96% ethanol for 10 minutes at ambient temperature.

After washing in TBS (Tris buffered saline), the cells, fixed as described above, were subjected to a blocking step with the aim of reducing the non-specific interactions of the antibody (i.e. reducing background noise).

The blocking step was conducted at ambient temperature for 15 minutes in goat serum at a concentration of 3% in TBS (Sigma).

As primary antibody a murine monoclonal antibody directed against human cytokeratin-19 (anti-human Cytokeratin, DAKO) was used, with the aim of determining the specific protein on the BM-MNCs.

The antibody was used at a dilution of 1:50 in PBS (initial concentration 21 mg/l, final concentration 0.42 mg/l) and the reaction between monoclonal antibody and the cells fixed on the slide was conducted overnight at 4° C.

Following this, the cells were washed with TBS in order to eliminate the non-bonded antibody. They were then incubated for 30 minutes at ambient temperature, with a secondary antibody (Alexa Fluor 488, Invitrogen) diluted 1:100 in PBS (initial concentration 2 mg/ml, final concentration 0.02 mg/ml).

The reading of the positive signal (i.e. the fluorescent cells) was performed using a confocal microscope. Before observing the cells under the microscope, TO-PRO (InVitrogen) was added, diluted at 1:7000 in distilled water, in order to mark the cell nuclei.

The images were collected and analysed using Interactive LCS software (Leica, Wetzlar, Germany).

The results, summarised in table 1 (BM-MNC CK-19$^+$) and in FIGS. 4-9, clearly demonstrate that all the sera of the individuals affected by carcinoma contain signals of tumoral origin which are capable of inducing differentiation of the mesenchymal cells in epithelial cells.

The serum originating from healthy individuals is not capable of inducing the in vitro differentiation of the mesenchymal stem cells in the epithelial sense. Only the serum of 3 normal individuals from a total of 12 individuals exhibited a very slight positivity (see samples S-6, 8 and 10).

The mesenchymal stem cells treated with the sera of healthy individuals under microscopic observation exhibit only the marked nucleus (FIGS. 1-3, black signal). No observation was made of cytoplasmic signal associable to cytokeratin 19 (see FIG. 1 (nuclear marking), FIG. 2 (CK-19 marking) and FIG. 3 (superposing of the two markings).

The mesenchymal stem cells treated with the sera of individuals affected by carcinoma exhibit a strong cytoplasmic signal (FIGS. 4-6 and relative enlargements of FIGS. 7-9, signal in colour grey) associable to cytokeratin 19, which surrounds the cell nucleus (figures 4 and 7 (nuclear marking), FIGS. 5 and 8 (CK-19 marking) and FIGS. 6 and 9 (superposing of the two markings).

Calculation of Specificity and Sensitivity of the Method.

The specificity of the method was calculated using the following equation:

Specificity=true negatives/total healthy=true negatives/(true negatives+False positives)

The sensitivity of the method was calculated using the following equation:

Sensitivity=true positives/total sick subjects=true positives/(true positives+False negatives)

For the method of the present invention, a sensitivity of 94.8% was calculated, and a specificity of 75%.

The invention claimed is:

1. A method for detecting one or more differentiation signals released into the circulation by a carcinoma comprising:
   (i) placing a culture of isolated bone marrow mononuclear cells into contact with a human haemo-derivative sample isolated from an individual, wherein said haemo-derivative is serum or plasma;
   (ii) maintaining the culture of step (i) for a suitable length of time to allow stem cells in the bone marrow mononuclear cell culture to express an epithelial marker; and
   (iii) detecting the epithelial marker in the cultured cells of step (ii).

2. The method of claim 1, wherein said epithelial marker is a cytokeratin.

3. The method of claim 2, wherein the cytokeratin is selected from the group consisting of: CK-18, CK-19, CK-20 and CK-21.

4. The method of claim 2, wherein the cytokeratin is CK-19.

5. The method of claim 1, wherein the serum or plasma is diluted with culture medium for bone marrow mononuclear cells prior to contact with said culture.

6. The method of claim 5, wherein the serum or plasma is diluted with the culture medium in a 1:2 to 1:20 ratio.

7. The method of claim 6, wherein the serum or plasma is diluted with the culture medium in a 1:4 to 1:8 ratio.

8. The method of claim 5, wherein the suitable length of time is from 48 to 180 hours.

9. The method of claim 8, wherein the suitable length of time is from 90 to 150 hours.

10. The method of claim 1, wherein in step (iii) the haemo-derivative is removed from the cells prior to detection of the epithelial marker.

11. The method of claim 1, further comprising a step of quantifying the amount of epithelial marker detected.

12. The method of claim 1, wherein the epithelial marker is detected by immunofluorescence or immunocytochemistry.

13. The method of claim 10, wherein the cells are subjected to lysis after the haemo-derivative is removed and prior to the detection of the epithelial marker.

14. The method of claim 13, wherein the epithelial marker is detected by ELISA or RT-PCR.

15. The method of claim 14, wherein the detection method is ELISA and the detected epithelial marker is quantified.

16. The method of claim 1, wherein said method further comprises prior to the detecting step, contacting the cultured cells of step (ii) with an antibody specific for said epithelial marker to form an antibody-epithelial marker complex.

17. The method of claim 16, wherein said detecting step comprises measuring the level of said antibody-epithelial marker complex.

* * * * *